United States Patent [19]

Hoborn et al.

[11] 4,321,925

[45] Mar. 30, 1982

[54] METHOD AND A DEVICE FOR CONTROLLING THE OCCURRENCE OF PERFORATIONS IN OPERATION GLOVES

[75] Inventors: Jan Hoborn, Askim; Ulrich Krebs, Harestad, both of Sweden

[73] Assignee: Molnlycke AB, Goteborg, Sweden

[21] Appl. No.: 91,488

[22] Filed: Nov. 5, 1979

[30] Foreign Application Priority Data

Nov. 9, 1978 [SE]  Sweden ................................ 7811560

[51] Int. Cl.³ ............................................. A61B 17/36
[52] U.S. Cl. ................................ 128/303.13; 361/224
[58] Field of Search ....................... 128/303.13, 303.14, 128/303.17, 303.18, 382, 383, 419 R; 174/5 SG; 361/223, 224, 88

[56] References Cited

U.S. PATENT DOCUMENTS

| 871,479 | 11/1907 | Cooper | 361/224 X |
| 3,544,841 | 12/1970 | Peel | 361/224 |
| 4,122,854 | 10/1978 | Blackett | 128/303.13 |
| 4,173,229 | 11/1979 | Halfon | 128/419 R |

FOREIGN PATENT DOCUMENTS

2450371 4/1975 Fed. Rep. of
 Germany ......................... 128/303.13

*Primary Examiner*—Lee S. Cohen
*Attorney, Agent, or Firm*—Holman & Stern

[57] ABSTRACT

The invention refers to an electronic detector arranged in such a way that the electric conductivity between e.g. a surgeon and a patient can be measured. The detector is preferably placed in the shoes of the surgeon and is through contact members on one hand connected to the surgeon's body and on the other hand to the bedding on which the surgeon stands, preferably a floor having a certain electric conductivity, or a round for this purpose. By the fact that an electrically conductive operating table is electrically connected to the same bedding also the patient will be galvanically connected with said bedding.

A detector arranged in this way can detect the conductivity between the surgeon and the patient and makes it possible to control possible biologic leakage, e.g. germ-containing liquid, through perforations in the operation gloves of the surgeon, at which infections in incisions can be avoided to a great extent.

6 Claims, 6 Drawing Figures

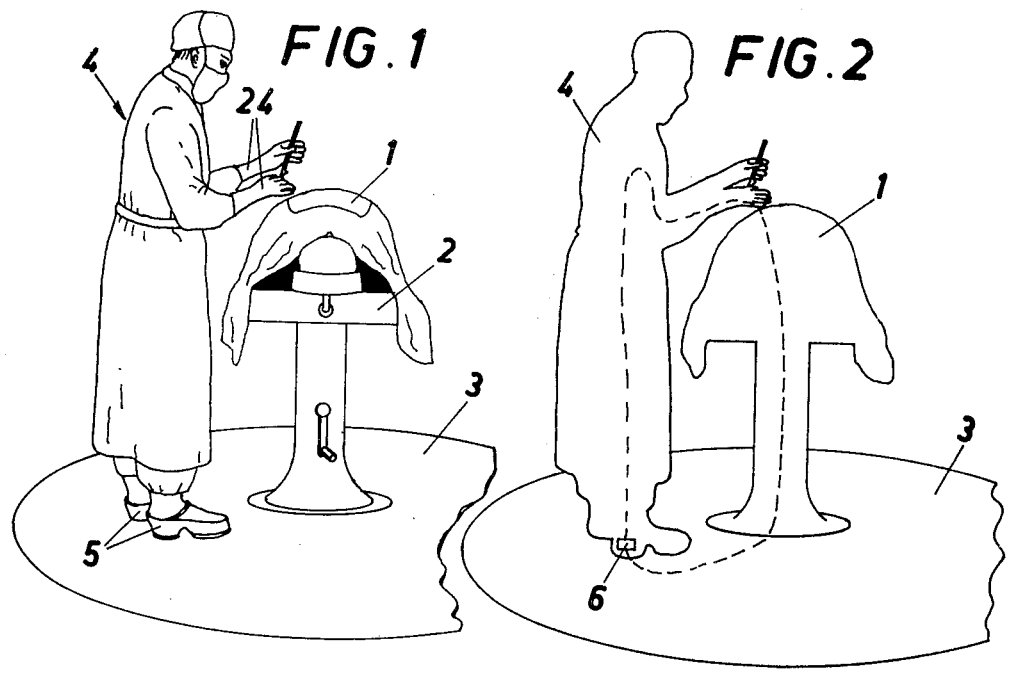
FIG.1
FIG.2
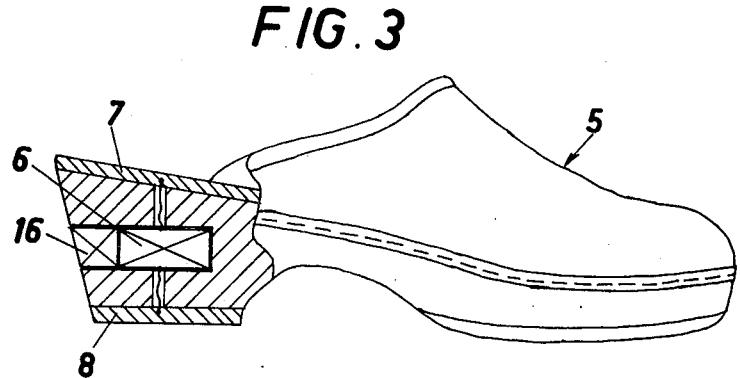
FIG.3
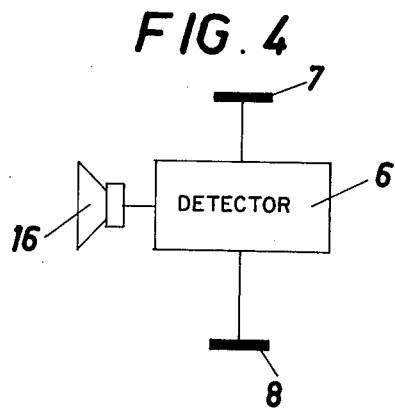
FIG.4

METHOD AND A DEVICE FOR CONTROLLING THE OCCURRENCE OF PERFORATIONS IN OPERATION GLOVES

BACKGROUND OF THE INVENTION

The invention refers to a method and a device for controlling and detecting the occurence of perforations in protective means, especially the surgical gloves of the operation staff.

In recent years a highly developed surgical operating technique has been developed. An increasing number of categories of patients are considered for surgical operations as e.g. transplants, heart operations, insertion of hip-, joint-, and knee prostheses. It has however been found that infections in the incisions often jeopardize the surgical results and the health of the patient. A strict aseptic technique is therefore of utmost importance.

Microorganisms and bacteria in the incision are the primary cause of the infections. These bacteria or microorganisms can come from the patient himself or from the closest surroundings as from the medical staff, the air or the medical requisites.

It is a well known fact that the medical staff are spreaders and transporters of infectious matters. In order to reduce the risk of infection the staff is for this reason dressed in tight working clothes. Operation clothes can today e.g. comprise a cap, mask, sterile operation coat and sterile surgical gloves. There have also been stipulated strict rules for the change of working-clothes under the sterile operation coat. There are also rules for how the washing of hands shall be accomplished in order to reduce as far as possible the number of microorganisms on and in the skin of the surgeon's hands. Despite this, and owing to the wearing of rubber gloves, there is a continuous transport of microorganisms together with sweat and tallow, from the pores up to the outer layers of the skin of the hand. On the inside of the operation gloves, a liquid which is very rich in bacteria and microorganisms is therefore accumulated in a relatively short time.

The surgical gloves are made as thin as possible so that the surgeon will have a good sensitivity but at the same time they have to be thick enough to last with the handling of sharp operating instruments and the like.

Tests have shown that in operations in soft tissues perforations, i.e. large or small holes, occur in about 40-50% of all operations. In orthopaedic surgery, where operations are made in bone tissues, perforations occur to an even greater extent, up to 95% of all operations. If a surgical glove is perforated during an operation there is a great risk that the bacteria-rich liquid accumulated in the operation glove will leak out through the perforation and into the incision. This often leads to undesired infections.

Devices for controlling surgical gloves are previously known in some cases. For example, in French patent specification No. 2.208.300 a device is described, with which perforations in surgical gloves can be detected. The device substantially comprises an electronic unit to which is connected a metal basin with an electrolyte and a junction arranged between the electronic unit and the surgeon. The idea is that the surgeon at certain intervals shall dip his hands into the metal basin, at which possible perforations are detected by the electric connection which occurs through these perforations.

This previously known device has a plurality of drawbacks of which only a number will be mentioned.

Firstly the surgeon has to be connected to the electronic unit through a conductor, which of course restricts the freedom of movement for the surgeon and which of course forms an obstacle to the assisting operation staff. Besides that the surgeon must remember at short and regularly recurrent intervals to interrupt the operation in order to dip his or her hands into the metal basin to detect possible perforations. At extensive and complicated operations this means of course a considerable drawback for the operation staff. It is further obvious that perforations can occur between the detection intervals, permitting bacteria to contiminate the incision.

Devices for discharging static electricity from surgeons, nurses etc. are also previously known. Such a device is described in the U.S. Pat. No. 3,544,841 and comprises a metal element connecting the inside of a footwear, e.g. a shoe, with the underside thereof, the sole. Owing to its design under certain unfortunate conditions, this device can instead of preventing cause spark formation in the operating room and, e.g., ignite anesthetic gases. This can, e.g., be the case when the surgeon does not stand in such a way that the sole and the device are not in contact with the floor. Static electricity will then accumulate in the body of the surgeon and this static electricity will be discharged causing spark formation when the surgeon changes position and the sole makes contact with the floor.

SUMMARY OF THE INVENTION

The object of the present invention is to provide a method for continuously controlling, detecting and indicating the occurence of perforations in operation gloves of e.g. a surgeon and to provide a cheap detector easy to handle, which during the operation controls and warns when perforations occur in the gloves of a surgeon. A further object of the invention is to discharge possible static electricity from persons using the invention regularly in order to avoid risks for explosions of anesthetic gases or similar. This is according to the invention achieved by the fact that the operator and an object, e.g. a patient treated by the operator, at least during regularly recurrent time intervals are electrically connected to an input each of the detector and that said detector senses and indicates changes of the electric conductivity between the operator and the operation object.

DESCRIPTION OF THE DRAWINGS

Some embodiments of the invention will now be further described with reference to the accompanying drawings.

FIG. 1 shows a surgeon working,

FIG. 2 shows an imaginary electric circuit,

FIG. 3 shows an operation shoe e.g. a clog, with a built-in detector,

FIG. 4 shows schematically the construction of the detector,

DESCRIPTION OF EMBODIMENTS

Figure 5:
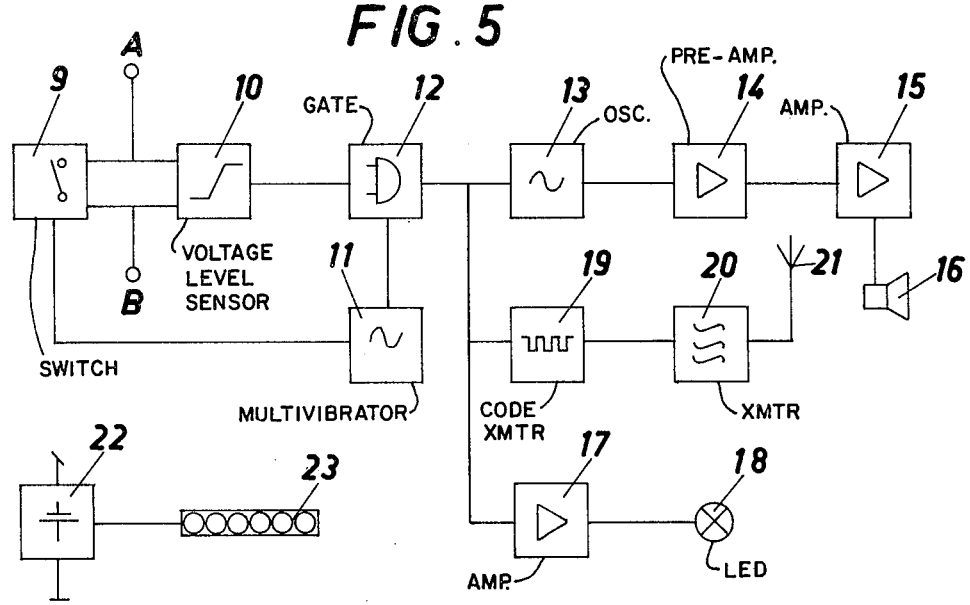
FIG. 5 shows a block diagram of the detector.

In FIG. 1 is shown how an operation object, e.g. a patient 1, is placed on an operating table 2, which is arranged on a round 3 placed on the floor. This round 3 is made by an, at least to a certain extent, electrically conducting material. A surgeon 4 dressed in operation clothes stands beside the table and operates the patient 1. The surgeon 4 is further provided with operation shoes 5, in which a detector 6 (shown in FIGS. 2 and 3) according to the invention is placed. The detector 6 is preferably arranged in the heel portion in one of the operation shoes 5, which e.g. can be a clog. The detector 6 is with a first input electrically connected with a first contact means located within the operation shoe 5 and can e.g. comprise an electrically semi-conducting or conducting insole 7. The detector 6 is with a second input also connected to the underside of the operation shoe 5, preferably an electrically semi-conducting or conducting bottom sole 8. This placing of the detector 6 means that the surgeon 4 is connected with the round 3 through the detector 6. The detector 6 arranged in the operation shoe 5 comprises a circuit of electronic components, an accumulator, an alarm device in the form of a light- and/or sound alarm and a set of solar cells for charging the accumulator.

In FIG. 5 the detector 6 is shown in detail in a block diagram. The insole 7 of the operation shoe 5 is here schematically denoted as a contact A and is on one hand connected to an electronic switch 9 arranged in the detector 6 and on the other hand with a voltage level sensor 10. The bottom sole 8 of the operation shoe 5 is here schematized as a contact B and is in the same way as contact A on one hand connected to the electronic switch 9 and on the other hand to the voltage level sensor 10. The electronic switch 9 is controlled by a multivibrator 11, which provides that the electronic switch 9 during regularly recurrent intervals is switched on and off. When the electronic switch 9 is switched on the contacts A and B are short-circuited with each other at which static electricity at contact A is discharged through contact B to the round 3. When the electronic switch 9 is switched off the voltage level sensor 10 senses the electric conductivity which occurs externally between the contacts A and B and when this electric conductivity exceeds a predetermined value a gate 12 arranged after the voltage level sensor is activated. The gate 12 activates a tone-oscillator 13 the output signal of which is amplified by a preamplifier 14 and a terminal amplifier 15. The output signal from the terminal amplifier 15 is delivered to a loud speaker 16, at which an alarm signal sounds. A light alarm can also be activated in parallel with this sound alarm. A further amplifier 17 connected to the gate 12 is then activated simultaneously with the tone-oscillator 13 and switches on a lamp or an illuminating diode 18. A further alarm is according to this described embodiment switched on simultaneously with the light- and sound alarm, but can of course replace the light- or sound alarm if so desired. This further alarm alternative comprises a code transmitter 19 and a transmitter 20 provided with an aerial 21. The code transmitter 19 is also actuated by the gate 12 and delivers a signal to the transmitter 20, so that the transmitter 20 through the aerial 21 emits a coded electromagnetic signal. The emitted signal is preferably received in an alarm unit (not shown) arranged centrally in the hospital and e.g. supervised by hospital personnel. One of the advantages of this system is that a plurality of surgeons in different operating rooms simultaneously and centrally can be supervised concerning perforations in the operation gloves 24 of the surgeons.

In order for detector 6 to work, electric energy has to be supplied. This can be made either by one or several rechargeable direct-current batteries or by one or several rechargeable accumulators 22. In this case accumulators 22 are used, at which solar cells 23 can be arranged in connection to the detector 6 and preferably in the operation shoe 5, so that the accumulators 22 are continuously charged and seldom or never have to be renewed. The solar cells 23 can be of such a type that they can utilize the light from the lighting in the operating room and converts this into electric energy, which is delivered to the accumulator 22. The accumulators can of course also be charged by connecting them to an external charging device when the operation shoes 5 are not used.

Figure 6:
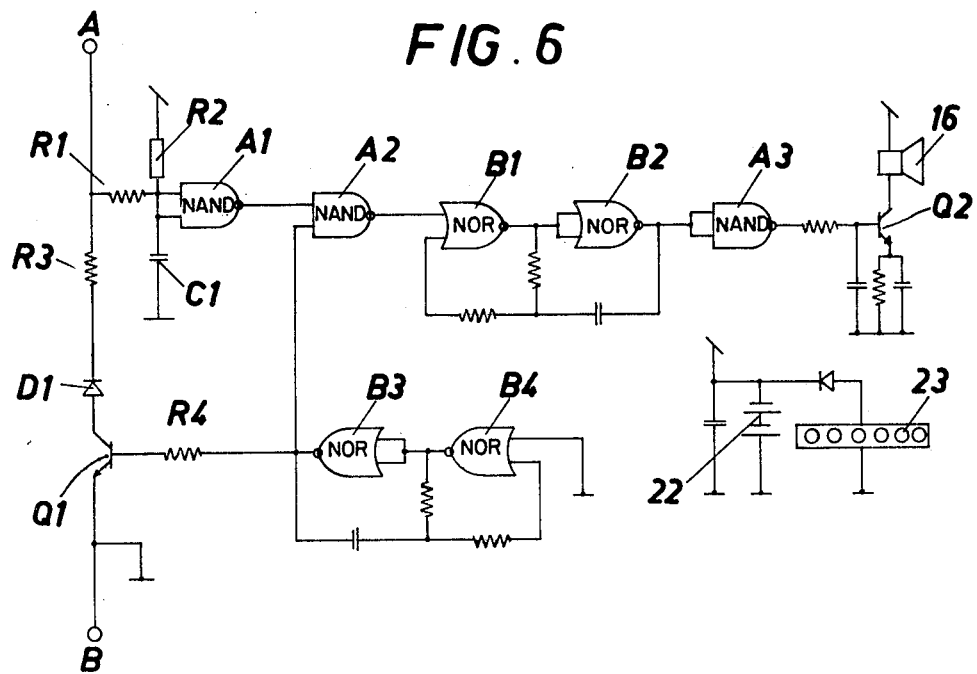
FIG. 6 shows a concrete circuit of the detector according to the invention.

In FIG. 6 is shown an example of a circuit for the above described detector 6. The detector 6 principally consists of integrated circuits of so called CMOS-type, which comprises a number of so called gates. The gates are partly so called inverted AND-gates (NAND) and partly so called inverted OR-gates (NOR). As tone oscillator 13 the gates B1 and B2 are used and its frequency has been chosen to about 2 kHz. Also the gates B3 and B4 are coupled as an oscillator and forms the multivibrator 11. The multivibrator preferably works with a frequency of about 5–10 Hz. When the transistor Q1 is actuated through the resistor R4 by the multivibrator the transistor Q1 starts conducting and admits electric energy with a voltage exceeding 7 V passing from the contact A through the resistor R3 and the Zener-diode D1 to the contact B. The oscillator B3, B4 controls besides the transistor Q1 also the gate A2. The gate A1 is through the resistor R1 connected to the contact A and through the resistor R2 to the plus pole of the accumulator 22. The inputs of the gate A1 are besides earthed through the capacitor C1. The resistor R2 has a high resistance and is intended to deliver a "high" voltage level to the input of the gate A1. Sice the gate A1 is of NAND-type this means that the output signal from the gate A1 has a "low" voltage level. When the contacts A and B are externally short-circuited with each other or if an electric conduction occurs the input voltage of gate A1 is changed and its output signal will have a "high" voltage level. If the oscillator B3, B4 at the same time delivers a high voltage level to the gate A2 the gate A2 delivers a "low" voltage level at its output. This involves that the oscillator, which comprises the gates B1 and B2, starts working.

The signal emitted by the oscillator B1, B2 is amplified in the gate A3 and in the transistor Q2 and is represented acoustically in the loud speaker 16.

The detector 6 is power supplied as previously mentioned by an accumulator 22 comprising two cells each with a voltage of 1.2 V, i.e. totally a voltage of 2.4 V. The accumulator is preferably compensating charged by a solar cell panel 23 through a diode.

The detector 6 operates in such a way that it 5 times per second short-circuits the contacts A and B, at which possible static electricity at the contact A is conducted to the contact B and further down to the bedding with which contact B is connected, preferably a floor. The voltage level sensor 10 is switched in with the same frequency, which means that the detector 6 about 5 times per second measures the external electric conductivity between the contacts A and B. If there is a perforation in the operation gloves 24 of the surgeon this involves that when the surgeon touches the body tissue of the patient there will be galvanic contact with a relatively high electric conductivity. The detector 6 emits then a light or a sound alarm. The external electric conductivity is thus measured by the detector 6 from the contact A through the surgeon's 4 body to the surgeon's hand skin and further through possible perforations in the operation gloves 24 to the operation portion of the patient 1. The body of the patient 1 and the operating table 2 or a ground connection (not shown) arranged for this purpose are galvanically connected with the at least to a certain extent electrically conductive floor or round 3, on which the surgeon 4 stands. When the operation shoe 5 with the detector 6 arranged therein contacts the floor or the round 3 there will thus be an external electric circuit (FIG. 2) from the contact A to the contact B on the detector 6. A change of the external electric conductivity between the contacts A and B from the one position, when there is no perforation and no contact between the surgeon and the patient and thus a practically indefinitely low conductivity, to the other position, when a perforation has occured in the operation gloves 24 resulting in that the surgeon 4 is galvanically connected to the patient and there is a relatively good conductivity, starts an alarm.

What we claim is:

1. A method for detecting perforations in a protective element, such as a surgical glove worn by an operator such as a surgeon, during the performance of an operation, such as surgery, on an object, such as a patient, said method comprising the steps of:

at regularly recurring time intervals during said operation, sensing the electrical conductivity through said operator, said protective element, and said object connected in series; and signaling an alarm in response to changes exceeding a predetermined level in said sensed conductivity.

2. The method according to claim 1 further including the step of periodically providing a discharge path to discharge static electricity across the series-connected operator, protective element, and object.

3. Apparatus for detecting and indicating perforations occurring in a protective element, such as a surgical glove, worn by an operator, such as a surgeon, said apparatus comprising:

voltage level sensor means, having two input terminals, for sensing electrical conductivity of external circuitry connected across said input terminals;

timed control means for, at regular intervals, connecting said protective element and said operator in series between said two input terminals; and alarm means responsive to the electrical conductivity sensed by said sensor means for providing a humanly perceptible signal when sensed conductivity exceeds a predetermined value.

4. The apparatus according to claim 3 further comprising:

a shoe having a heel portion which is adapted to be worn by said operator;

wherein said voltage level sensor means, said timed control means and said alarm means are disposed in said shoe, preferably in said heel portion; and wherein said shoe includes an insole contact and an underside contact to which said two input terminals are connected, respectively, at said regular intervals by said control means.

5. The apparatus according to claim 4, wherein said contacts comprise an at least electrically semi-conductive material, said insole contact at least partly covering an inner surface and said underside contact at least partly covering an outer bottom surface of the shoe.

6. The apparatus according to claim 3, further comprising electronic switch means for periodically electrically connecting together said two inputs in order to discharge static electricity.

* * * * *